United States Patent
Fuhrmann et al.

(10) Patent No.: US 9,720,512 B2
(45) Date of Patent: Aug. 1, 2017

(54) DEVICE AND METHOD FOR THE GESTURE-CONTROLLED SETTING OF SETTING VARIABLES ON AN X-RAY SOURCE

(71) Applicant: SIEMENS AKTIENGESELLSCHAFT, Munich (DE)

(72) Inventors: Michael Fuhrmann, Herzogenaurach (DE); Anja Jaeger, Fuerth (DE); Robert Kagermeier, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 5 days.

(21) Appl. No.: 14/736,493

(22) Filed: Jun. 11, 2015

(65) Prior Publication Data

US 2015/0363002 A1 Dec. 17, 2015

(30) Foreign Application Priority Data

Jun. 11, 2014 (DE) .................. 10 2014 211 115

(51) Int. Cl.
*G06F 3/01* (2006.01)
*G06F 3/0487* (2013.01)
*A61B 6/00* (2006.01)

(52) U.S. Cl.
CPC .............. *G06F 3/017* (2013.01); *A61B 6/465* (2013.01); *A61B 6/467* (2013.01); *G06F 3/0487* (2013.01)

(58) Field of Classification Search
USPC .................. 378/206, 95, 65, 8, 102
See application file for complete search history.

(56) References Cited

U.S. PATENT DOCUMENTS

| | | | | |
|---|---|---|---|---|
| 5,981,965 A * | 11/1999 | Pryor | .................. | G01B 11/002 250/208.1 |
| 8,817,085 B2 | 8/2014 | Hiltl et al. | | |
| 8,965,583 B2 * | 2/2015 | Ortmaier | .................. | B25J 13/00 345/168 |
| 2015/0043712 A1 * | 2/2015 | Wang | .................... | A61B 6/022 378/42 |
| 2015/0253865 A1 * | 9/2015 | Hayashi | ................. | A61B 6/467 600/436 |
| 2015/0351709 A1 * | 12/2015 | Dirauf | .................... | A61B 6/545 378/206 |

FOREIGN PATENT DOCUMENTS

| | | |
|---|---|---|
| DE | 19845028 A1 | 6/2000 |
| DE | 102012205549 A1 | 10/2013 |
| EP | 2283790 A1 | 2/2011 |

* cited by examiner

*Primary Examiner* — Phillip A Johnston
(74) *Attorney, Agent, or Firm* — Laurence Greenberg; Werner Stemer; Ralph Locher (57) ABSTRACT

A device for the gesture-controlled setting of at least one setting variable on an X-ray source includes at least one recognition unit for anatomically recognizing a body part suitable for gesture control, at least one gesture detection unit for detecting at least one gesture of a body part recognized by the recognition unit, and at least one light source for displaying the at least one setting variable as feedback for a person making the gesture. The at least one setting variable was preset and/or set by using the at least one detected gesture. A method for the gesture-controlled setting of at least one setting variable on an X-ray source is also provided.

8 Claims, 8 Drawing Sheets

DEVICE AND METHOD FOR THE GESTURE-CONTROLLED SETTING OF SETTING VARIABLES ON AN X-RAY SOURCE

CROSS-REFERENCE TO RELATED APPLICATION

This application claims the priority, under 35 U.S.C. §119, of German Patent Application DE 10 2014 211 115.3, filed Jun. 11, 2014; the prior application is herewith incorporated by reference in its entirety.

BACKGROUND OF THE INVENTION

Field of the Invention

The invention relates to a device and a method for the gesture-controlled setting of one or a plurality of setting variables on an X-ray source of an imaging apparatus.

The invention is predominantly in the fields of medical technology and medical information technology. Other applications, such as e.g. in industry, are also conceivable. In this regard, the invention could also be used, if appropriate, in materials testing or baggage inspection or generally in equipment operation.

One field of application is in the field of radiology, in which computer-aided RIS (abbreviation of the designation "Radiology Information System"), HIS (Hospital Information System), KIS (German abbreviation of Hospital Information System) and PACS (abbreviation of the designation "Picture Archiving and Communication System") systems are usually used. Radiology is based on image acquisition on different modalities or medical imaging apparatuses such as e.g. a computed tomography apparatus (CT), a magnetic resonance imaging apparatus (MRI), a positron emission tomography apparatus (PET), an X-ray apparatus, or an ultrasound apparatus (US). The radiological examination apparatuses mentioned provide the image data record. The image data record is generally an image volume data record containing a volume image, or an image series data record containing a series of images.

In the context of medical imaging and/or treatment apparatuses such as e.g. X-ray or C-arm apparatuses, for various reasons provision may be made for determining the position of the patient and/or of other objects, in particular the spatial treatment and/or examination region of the patient, at least partly and/or at least approximately.

The use of laser projection is possible in the case of X-ray apparatuses. For visually checking a treatment or examination region in radiology, a light source, preferably a laser, is conventionally used which projects laser markings onto the patient, which are verified by using an image recording.

A diaphragm is usually used for setting the examination region to be irradiated during X-ray examinations, the diaphragm being fitted directly to the tube. The insertion can be varied by using integrated, displaceable lead lamellae in order to ensure that only the regions actually of interest are irradiated and the scattered radiation can also be minimized. A light source is used for visualizing this insertion, the light from the light source being diverted through a mirror in such a way that the visible light corresponds to the course of the beam path and represents on the patient where X-ray radiation that is invisible during the recording will impinge.

Therefore, even before the actual irradiation, the user switches on the light source e.g. using a knob on the diaphragm and turns rotary knobs until the lead lamellae insert the desired examination region. In order to ensure that the built-in luminaire is not left switched on continuously, an automatic, time-controlled switch-off can be provided. It is therefore possible for the insertion to actually be switched off while the user would like to carry out settings on the system, and it therefore has to be switched on again.

In order to additionally enable the correct exposure time for an optimum image quality in conjunction with low radiation loading in the case of X-ray recordings, measuring chambers are incorporated in the detector. The measuring chambers measure the radiation behind the X-rayed patient and automatically switch off the generator as soon as the necessary exposure value is attained.

In general, in present-day detectors, the region at which the measuring chambers are situated ("measurement field") is fixedly defined with regard to size and position and the user can only choose between predefined measurement fields. That construction is not very flexible, since the measurement fields have to be used for different types of recording with different patients. A bone examination for an adult patient normally requires different examination parameters than a lung examination for a newborn. The detectors and measuring chambers used nowadays only satisfy those different requirements to a limited extent.

Fixed measurement fields are available at the apparatuses and their position cannot be altered arbitrarily. Instead, the entire detector has to be positioned so accurately that the region of interest of the patient is situated in front of the measurement field and is thus exposed as well as possible.

SUMMARY OF THE INVENTION

It is accordingly an object of the invention to provide a device and a method for the gesture-controlled setting of setting variables on an x-ray source, which overcome the hereinafore-mentioned disadvantages of the heretofore-known devices and methods of this general type and which develop an improved technology for an imaging X-ray apparatus.

With the foregoing and other objects in view there is provided, in accordance with the invention, a device for the gesture-controlled setting of one or a plurality of setting variables, e.g. examination parameters, on an X-ray source, comprising:
at least one recognition unit for anatomically recognizing a body part suitable for gesture control,
at least one gesture detection unit for detecting at least one gesture of a body part recognized by the recognition unit,
at least one light source for displaying the setting variables as feedback for a person making the gesture,
wherein the setting variables were preset and/or set by using the at least one detected gesture.

In this case, the setting variables can be automatically adapted to the recognized object to be examined and/or can preferably be optically displayed thereon with the aid of the light source. The setting variables can include a signal for activating/deactivating a light source. They can also represent diaphragm settings, exposure settings. They can also include parameters for setting a radiation measurement field or the displaying, shaping and positioning of such a measurement field or other examination parameters. The feedback can be not just the straightforward display of such setting variables. It can also include insertions and/or maskings and/or activation and/or deactivation as reaction to the one or the plurality of detected gestures.

The recognition unit can be constructed as a depth camera. The recognition unit can be constructed in such a way that it anatomically recognizes an object to be examined. The recognition unit and the gesture detection unit can be combined in one unit.

The body part to be recognized can be a hand or else just fingers or an arm. Free hand gestures, arm gestures, head gestures or eye movements and touchpad-like gestures can be used as gestures. A beamer and/or a projector are/is conceivable as a light source.

With the objects of the invention in view, there is also provided a method for the gesture-controlled setting of one or a plurality of setting variables on an X-ray source, comprising the following steps:
anatomically recognizing a body part suitable for gesture control,
detecting at least one gesture of a recognized body part,
projecting the setting variables for displaying the same as feedback for a person making the gesture,
wherein the setting variables were preset and/or set by using the at least one detected gesture.

The developments concerning the device are correspondingly applicable to the method.

With the aid of the invention, the user can save one of the work steps for inputting the examination region, since the system automatically recognizes if a gesture-based input is intended to be carried out, and reacts accordingly by switching on the light source.

In this way, during preparation for the examination, the user can remain directly beside the patient in order to support or correctly position the patient, for example, and can carry out all necessary steps in proximity to the patient. The user does not then have to go to the diaphragm in order to input the insertion there.

Further work steps—centering the tube over the detector, and setting the insertion can furthermore be combined. In this way, the work sequence is accelerated and becomes easier for the user since an optimum positioning is carried out automatically.

The incorporation of a projector can afford diverse possibilities of interaction which the user can perform in proximity to the patient.

The user can even be in direct, including physical, contact with the patient (for example for scanning the vertebral column), in order to be able to position the addressed measurement field at the same time. The optimized possibility of setting the measurement field makes it possible to obtain images which are well exposed and therefore contribute to reliable findings. In this case, the interaction with the system is intuitive and easy to learn. The insertion reacts in real time to the input gestures of the user, in such a way that reliable handling is ensured.

Other features which are considered as characteristic for the invention are set forth in the appended claims.

Although the invention is illustrated and described herein as embodied in a device and a method for the gesture-controlled setting of setting variables on an x-ray source, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
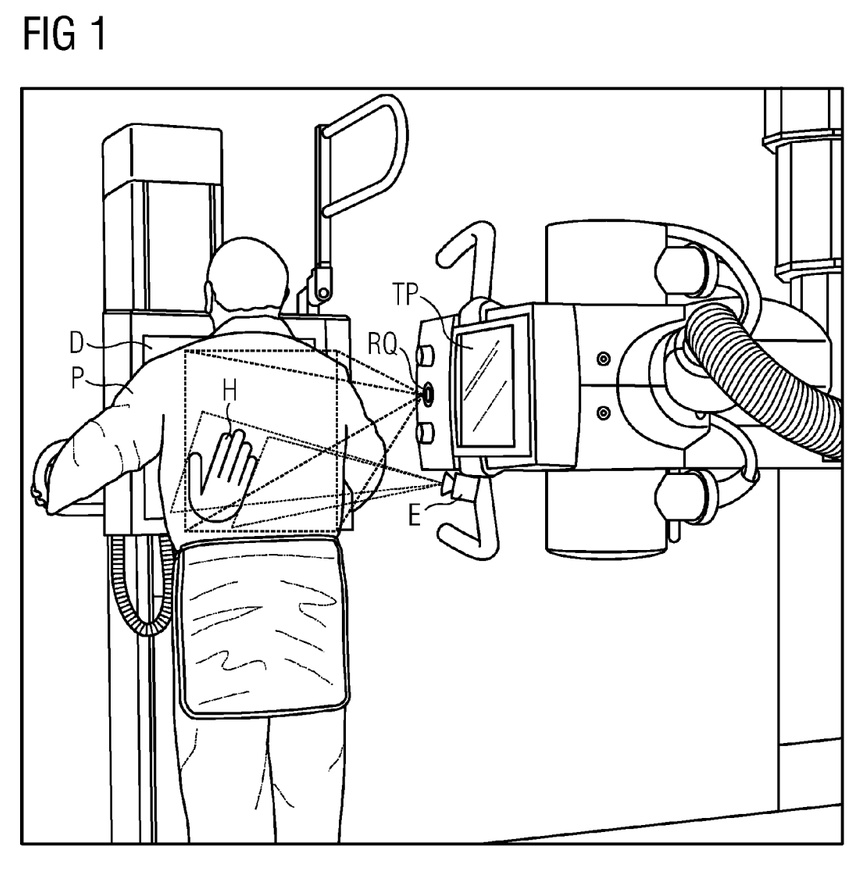
FIG. 1 is a diagrammatic, perspective view of an embodiment of the invention which allows a light insertion to be switched on and off automatically at an X-ray tube.

Referring now to the figures of the drawings in detail and first, particularly, to FIG. 1 thereof, there is seen, by way of example, a construction of a medical imaging instrument or apparatus, e.g. an X-ray apparatus. However, the invention is not restricted thereto. Such an apparatus has at least one X-ray tube or X-ray radiation source RQ with an oppositely-disposed detector D. The X-ray source and the detector are disposed in such a way that a patient P who is to be penetrated by X-ray radiation can be supported or placed between the X-ray source and the detector. X-ray radiation generated by the X-ray source penetrates through the patient P and is detected at a detector after penetrating through the patient.

The apparatus can furthermore include measures (not shown in the drawing) which are suitable for carrying out the method according to the invention.

A non-illustrated computing unit is often used for controlling the apparatus. The control itself and the read-out of detector output data take place through a control and data line connected to the computing unit. An operating device TP, e.g. a touch screen or touch panel or a touchpad for a user, is provided at the computing unit.

Figure 2:
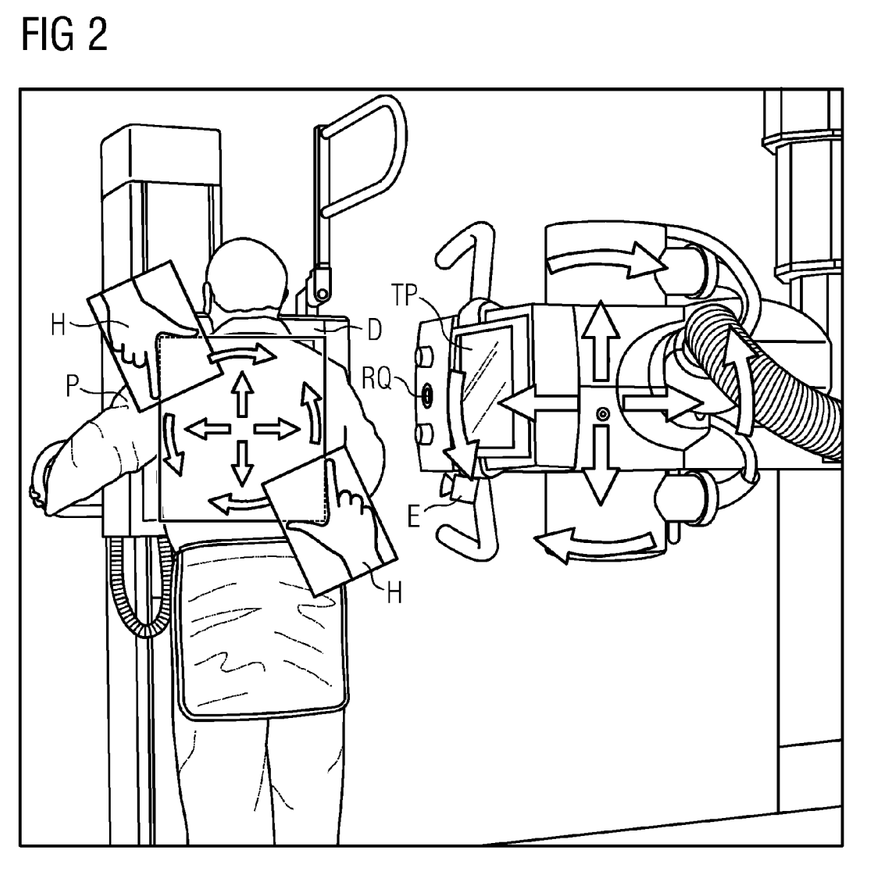
FIG. 2 is a perspective view of an embodiment of the invention in which a gesture-controlled inputting of an examination region is made possible.

FIG. 2 furthermore indicates an examination or treatment region OG of a patient. The patient P is generally covered with a sterile cover.

Furthermore, one or a plurality of optical detection units E e.g. in the form of a camera can be fitted to the apparatus, preferably on the X-ray source side. In the exemplary embodiment, functions of a recognition unit, e.g. a camera that recognizes spatial depth, for anatomically recognizing a body part suitable for gesture control, e.g. a hand H, and functions of a gesture detection unit are combined in one optical detection unit. It is also possible to fit separate units for the two mentioned functions near the X-ray source RQ.

Figure 3:
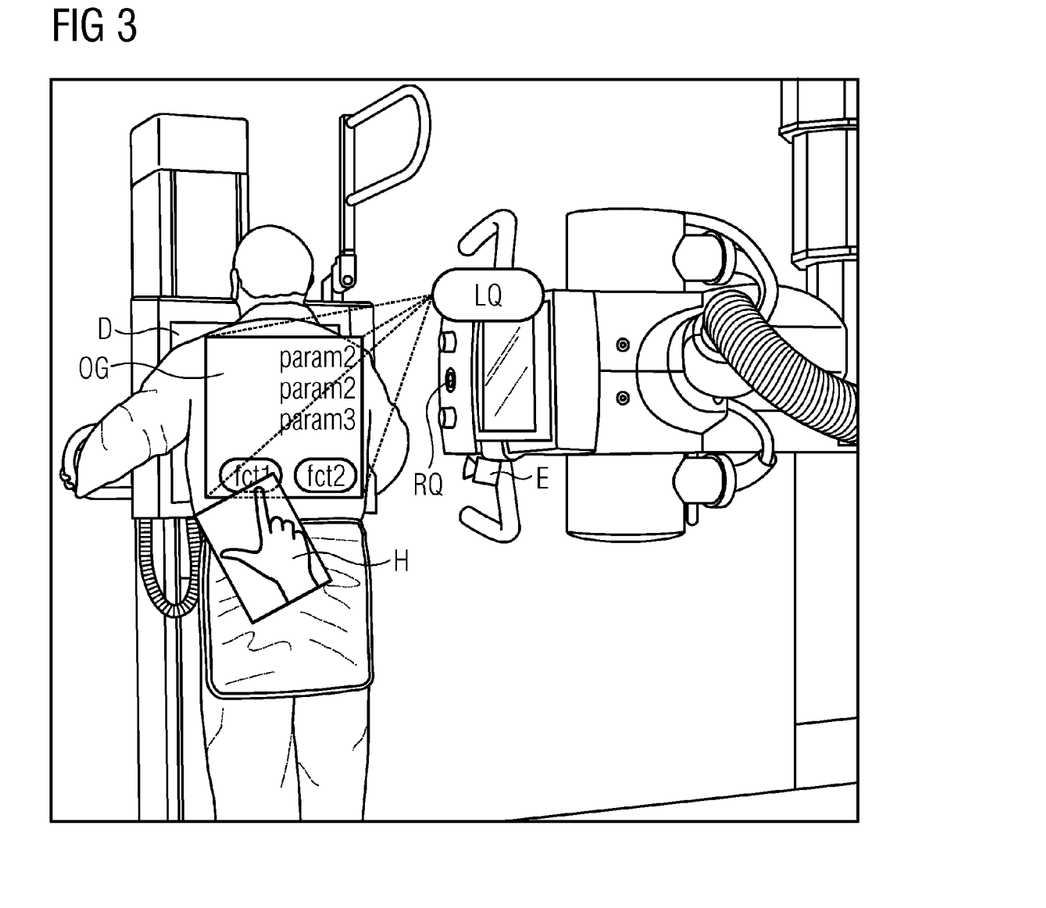
FIG. 3 is a perspective view of an embodiment of the invention in which usable functions and examination parameters can be inserted and selected directly at the patient.

FIG. 3 shows how a hand H is recognized, for example, which allows light insertion by a light source LQ to be switched on and off automatically at an X-ray source RQ. As soon as a hand is recognized below the diaphragm, the light for the insertion is automatically switched on or off. For this purpose, a detection unit, e.g. a (depth) camera, which continuously monitors the space in the direction of the beam path, is incorporated in the diaphragm. All objects that stay in the camera's field of view are checked with regard to their similarity to the anatomy of a hand. If a hand H is detected below the diaphragm, then the intention of the user A (see FIG. 6) to alter the insertion is also taken as a basis and the light insertion is automatically activated. As soon as the hand disappears from the field of view, that is to say that accordingly no further interaction is intended to take place, the light source is deactivated.

FIGS. 2 to 5 show by way of example how a method can be performed which optimizes the work sequence at the X-ray apparatus by using gesture control, wherein centering and insertion are carried out in a single step.

For this purpose, there is installed on the apparatus at least one detection unit E, e.g. a camera, which is suitable for detecting the position of the user A in the room and for recognizing the position of the user's hands H. By way of example, it is possible to choose one camera in the room for localizing the user, and a further camera on the X-ray tube for recognizing the hands.

In an embodiment with only one camera on the X-ray source, the latter is coarsely prepositioned by the user A, in such a way that it already faces in the direction of the detector D. The desired insertion is subsequently indicated by the hands—as portrayed in FIG. 5. The X-ray source is tracked by motor in real time and is centrally positioned continuously depending on the area indicated. At the same time, lead lamellae are tracked in such a way that the insertion corresponds to the area indicated. The size and position of the area can be varied arbitrarily by the user A indicating the change with the hands. The integration of a projector instead of the conventional light source LQ in the diaphragm is conceivable for more diverse possibilities of interaction. The user can then be given visual feedback with regard to the user's actions that goes beyond the mere light insertion. In this regard, examination parameters param1, param2, param3 and functions fct1, fct2, for example recording data or organ programs, can be displayed, which can be selected on the screen. As indicated in FIG. 4, for this purpose the integrated camera recognizes click gestures or time-controlled input methods, for example, and assigns them to the corresponding option.

Figure 4:
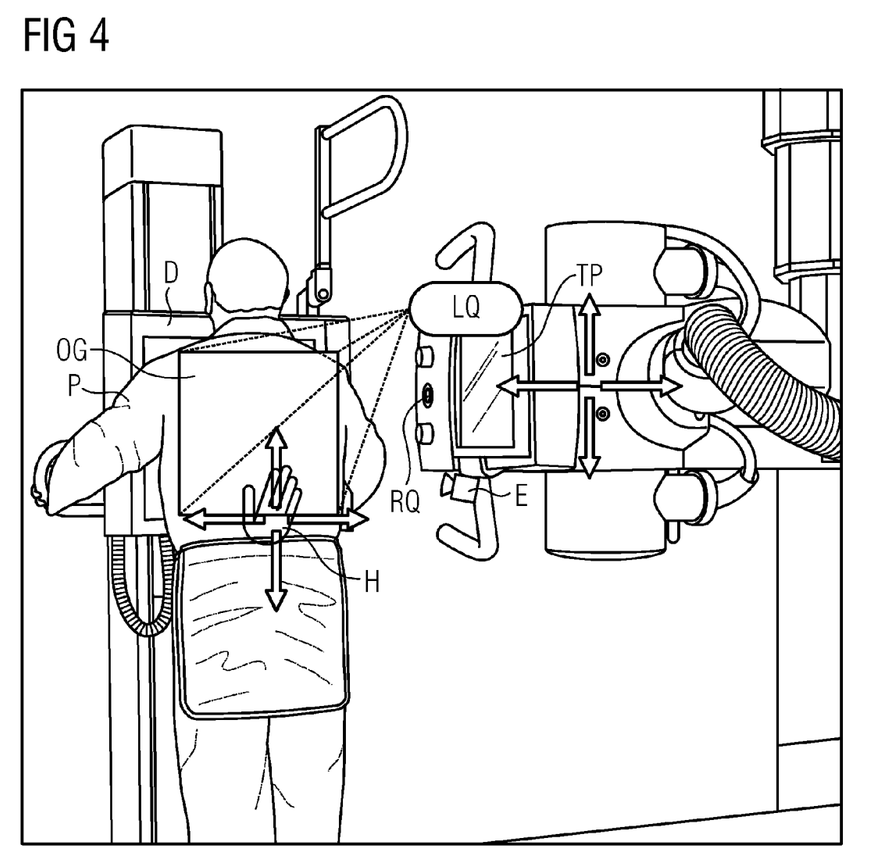
FIG. 4 is a perspective view of an embodiment of the invention in which an insertion by a light source, in particular by a light source LQ, is displaceable.
Figure 5:
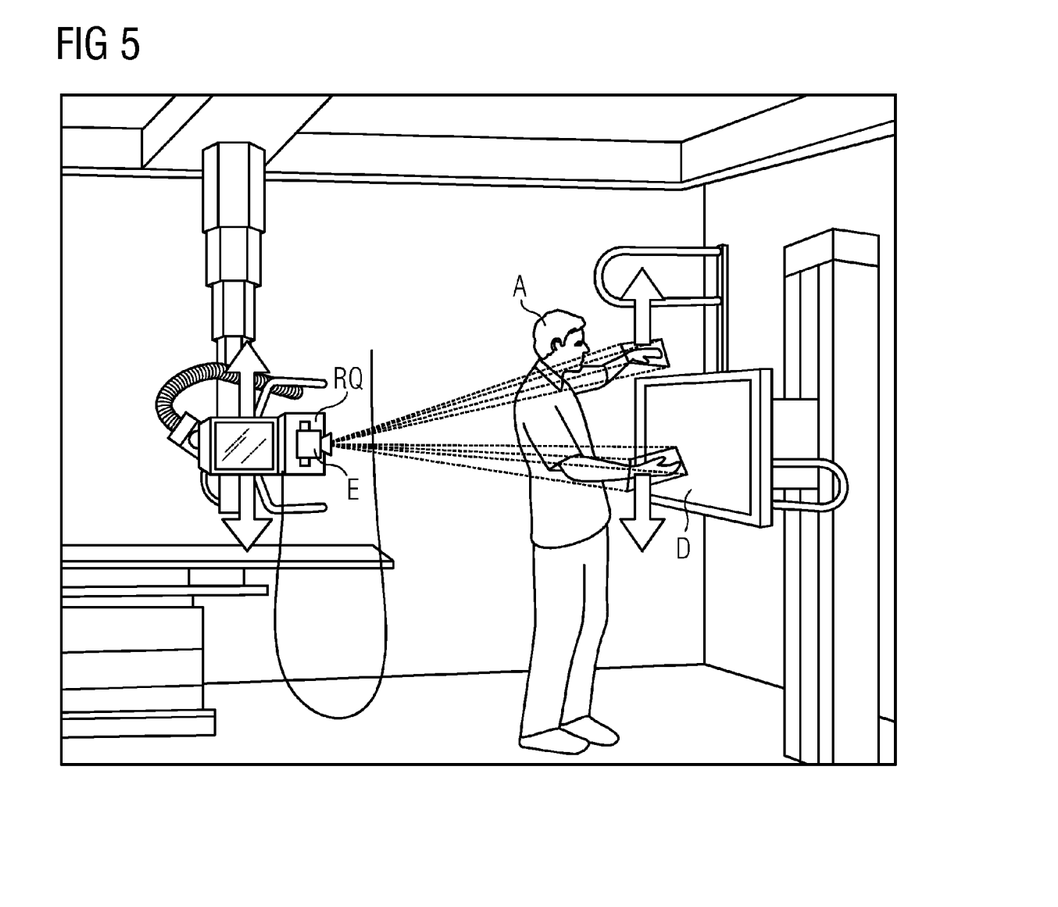
FIG. 5 is a perspective view of an embodiment of a gesture detection unit.

An embodiment, indicated in FIG. 4, is conceivable which makes it possible to record the light insertion with only one hand, in order to subsequently displace the insertion, but to maintain the size. In this case, the position of the X-ray source is likewise tracked automatically—as described above.

In an embodiment with at least one further camera for room monitoring, a similar sequence is also conceivable without prepositioning. The user's position in the room is recognized. As soon as an indication of the examination region OG is also evident, the X-ray source is positioned accordingly. With the camera in the X-ray source, the further alignment is carried out in a manner analogous to that described above. For safety release for the apparatus movement, it is possible to use a cable-based or wireless foot-operated switch/manual operating unit ensuring secure signal transmission.

Figure 6:
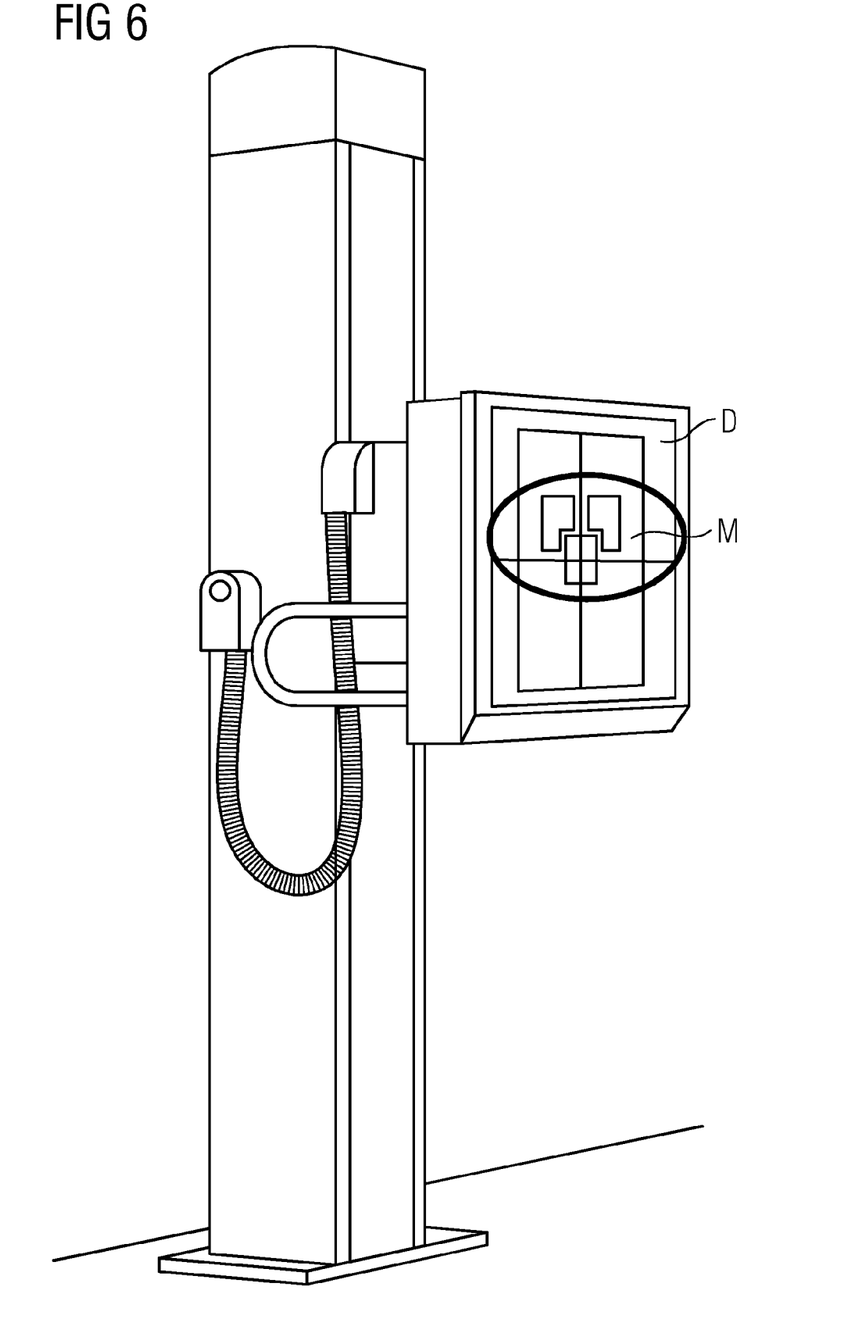
FIG. 6 is a perspective view of prior art (radiation) measurement fields at a customary detector for detecting X rays.
Figure 7:
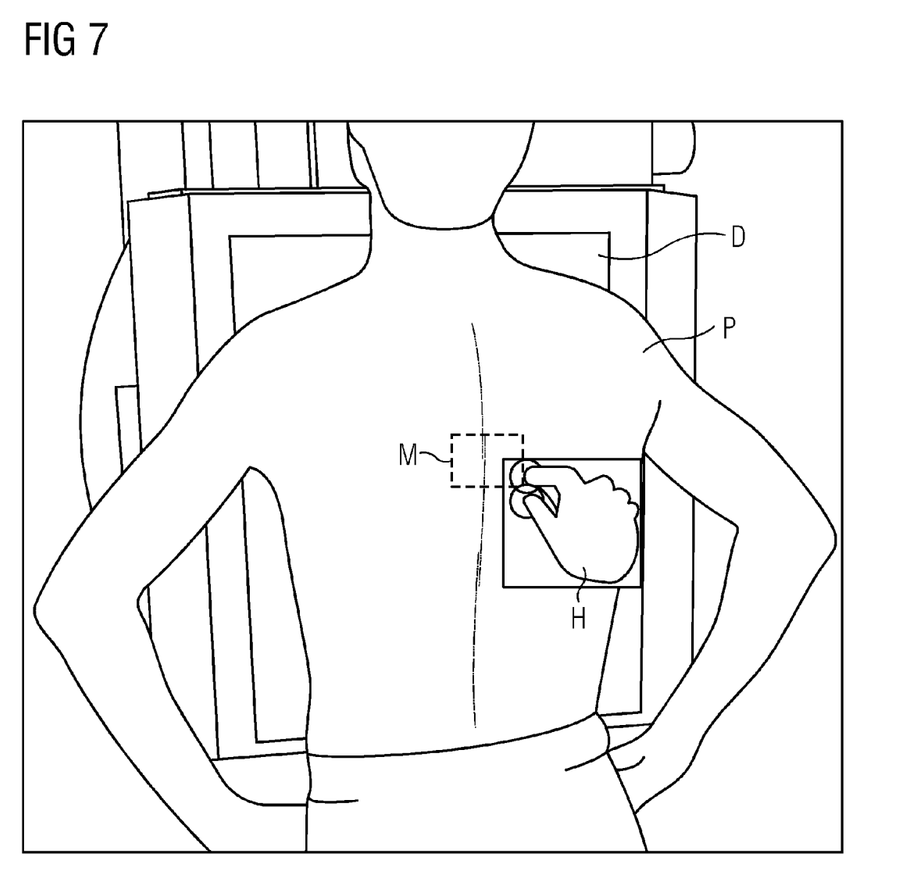
FIG. 7 is a perspective view of an embodiment of the invention in which the measurement field can be adapted by a gesture.
Figure 8:
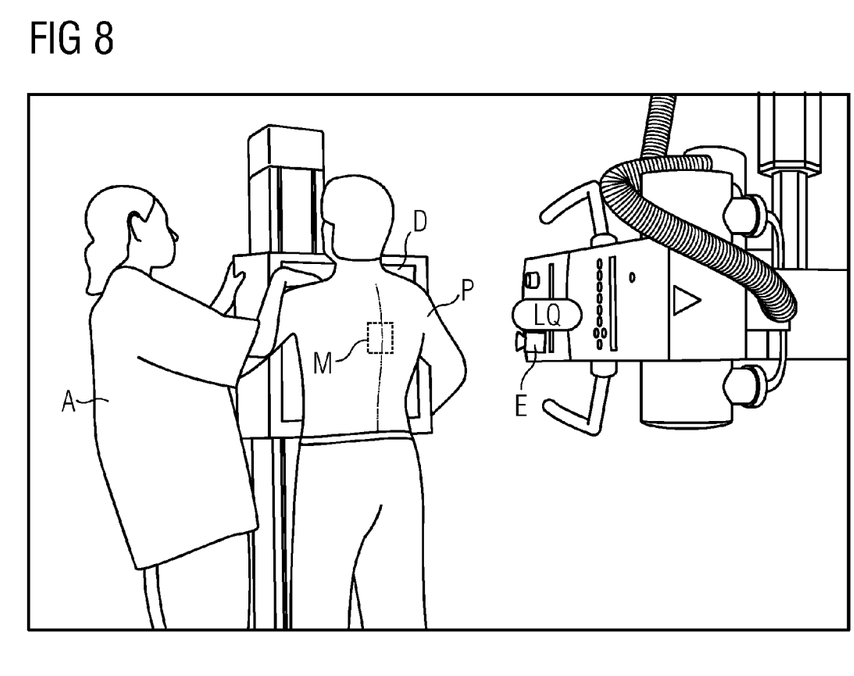
FIG. 8 is a perspective view of an exemplary construction of a medical imaging apparatus in which a measurement field is inserted directly at the patient.

FIGS. 6 to 8 show embodiments which allow the addressed measurement field to be shaped and positioned arbitrarily.

FIG. 6 shows in this respect measurement fields at a customary detector for detecting X-rays.

A stored measurement field M is projected by using a light source LQ, in particular a beamer or projector, directly from the diaphragm onto the patient and can be adapted in real time by the user by using freehand gestures. The adaptation is carried out by using simple finger gestures which are detected and evaluated by a detection unit, e.g. a depth camera, and by using which the object is grasped, displaced or enlarged. The interaction is intuitive since the type of operation is very close to that of a touchpad and the user receives direct feedback by virtue of the projector insertion.

An embodiment is conceivable in which the patient's body is detected and anatomically correctly recognized by a camera. The preset measurement fields M can then already be projected onto the correct location in accordance with the selected examination, in such a way that the user need only perform a fine adjustment.

This procedure is well suited for example to recordings on the Bucky wall unit since the measurement field M exactly itself—as indicated in FIG. 7—can be set to individual vertebrae. For pediatrics, too, the use of very small measurement fields opens up new possibilities.

FIG. 8 shows the construction of the overall system with a detection unit for detecting the user's hand and a projector for inserting the measurement fields.

Detectors with a variable measurement field are provided. This can be realized with an explicit high-resolution measurement field matrix in addition to the flat panel detector. Alternatively, it is also conceivable for corresponding regions of the flat panel detector to be used for measurement, wherein a continuously readable detector or a method for pre-exposure by using X-ray pulses is expedient for this purpose.

The invention claimed is:

1. A device for the gesture-controlled setting of at least one setting variable on an X-ray source, the device comprising:
    at least one recognition unit for anatomically recognizing a body part suitable for gesture control;
    at least one gesture detection unit for detecting at least one gesture of a body part recognized by said recognition unit;
    at least one light source configured to project the at least one setting variable for optical display on the object to be examined as feedback for a person making the gesture; and
    the at least one setting variable being at least one of preset or set by using the at least one detected gesture.

2. The device according to claim 1, wherein said recognition unit is configured to anatomically recognize an object to be examined.

3. The device according to claim 2, wherein the at least one setting variable can be automatically adapted to the recognized object to be examined with the aid of the light source.

4. The device according to claim 1, wherein said recognition unit and said gesture detection unit are combined in one unit.

5. The device according to claim 1, wherein the at least one setting variable represents parameters for setting a radiation measurement field.

6. A method for the gesture-controlled setting of at least one setting variable on an X-ray source, the method comprising the following steps:
    anatomically recognizing a body part suitable for gesture control;

detecting at least one gesture of a recognized body part;
projecting the at least one setting variable for optical display on the object to be examined to provide feedback to a person making the gesture; and
at least one of presetting the at least one setting variable or setting the at least one setting variable by using the at least one detected gesture.

7. The method according to claim 6, which further comprises automatically adapting the at least one setting variable to a recognized object to be examined with the aid of a light source.

8. The method according to claim 6, wherein the at least one setting variable represents parameters for setting a radiation measurement field.

\* \* \* \* \*